United States Patent [19]

Hosono et al.

[11] Patent Number: 5,789,439
[45] Date of Patent: Aug. 4, 1998

[54] PHARMACEUTICAL USE OF FORSKOLIN DERIVATIVES

[75] Inventors: Makoto Hosono, Kitamoto; Akira Fujita, Omiya; Giichi Izumi; Tochiro Tatee, both of Tokyo; Takashi Takahira, Yono; Yasuhiko Furuta, Saitama-ken; Michiko Sakai; Osamu Ishizuka, both of Tokyo; Takashi Terada, Konosu; Junpei Itoh, Yono, all of Japan

[73] Assignee: Nippon Kayaku Kabushiki Kaisha, Tokyo, Japan

[21] Appl. No.: 861,262

[22] Filed: May 21, 1997

Related U.S. Application Data

[63] Continuation of Ser. No. 425,217, Mar. 16, 1995, abandoned, which is a continuation of Ser. No. 179,366, Jan. 10, 1994, abandoned, which is a division of Ser. No. 5,863, Jan. 13, 1993, abandoned, which is a continuation of Ser. No. 670,063, Mar. 15, 1991, abandoned.

[30] Foreign Application Priority Data

| Mar. 23, 1990 | [JP] | Japan | 2-72022 |
| Mar. 23, 1990 | [JP] | Japan | 2-72023 |
| Jun. 12, 1990 | [JP] | Japan | 2-151552 |
| Jun. 15, 1990 | [JP] | Japan | 2-155108 |

[51] Int. Cl.$^6$ .................................................. A61K 31/35
[52] U.S. Cl. .................................................. 514/455
[58] Field of Search .................................................. 514/455

[56] References Cited

U.S. PATENT DOCUMENTS

| 4,873,227 | 10/1989 | Ikada et al. | 514/47 |
| 4,909,799 | 3/1990 | Thulesius et al. | 604/265 |
| 4,954,642 | 9/1990 | Tatee et al. | 514/455 |

FOREIGN PATENT DOCUMENTS 8503637  8/1985  WIPO.

OTHER PUBLICATIONS

An 88-331310 (WPIDS) Dreher et al, "Tri-terpene forskoline use—for acceleration of epithelial all growth in tissue culture", corresponding to EP 291696, Abstract only, Nov. 23, 1988.
Medicinal Research Reviews, vol. 3, No. 2, Apr.–Jun. 1983, pp. 201–219, N.J. DeSouza, et al.
Biochemical Pharmacology, vol. 31, No. 24, 1982, pp. 4071–4074, S. Adnot et al.
Molecular Pharmacology, vol. 32, No. 1, 1987, pp. 133–139, A. Laurenza, et al.
Molecular Pharmacology, vol. 31, No. 3, May 1982, pp. 680–687, A.M. Siegl, et al.
Naunyn–Schmiedeberg's Archives of Pharmacology, vol. 331, No. 1, 1985, pp. 119, 121, T. Kariya, et al.
Medical Science Research, vol. 16, No. 19, 1988 pp. 1027–1028.
Reserach in Experimental Medicine, vol. 190, No. 3, 1990 pp. 223–227.
Journal of Dermatological Science, vol. 1, No. 1, Jan. 1990 pp. 7–14.
Molecular Pharmacology 21; 680–687, Jan. 1982.
Arzneimittel–Forschung, vol. 31, pp. 1248–1250 (1981).
Journal of Medical Chemistry, vol. 26 (1983) pp. 486–492.
International Patent Appln. Publication No: WO 85/03637 (Aug. 29, 1985).

*Primary Examiner*—Keith MacMillan
*Attorney, Agent, or Firm*—Nields, Lemack & Dingman

[57] ABSTRACT

The present invention relates to novel pharmaceutical use of forskolin derivatives represented by the general formula:

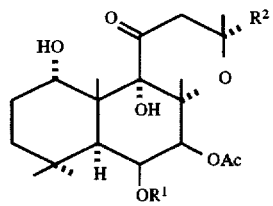

wherein $R^1$, $R^2$ and Ac are as defined later

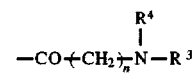

(wherein $R^3$ and $R^4$ are each hydrogen or lower alkyl group, or $R^3$ and $R^4$ may be combined to represent lower alkylene group which may have oxygen or nitrogen atom in the linking chain, and n is an integer of 1 to 5); $R^2$ represents hydrocarbon group having 2 to 3 carbon atoms; and Ac represents acetyl group.

The above-mentioned forskolin derivative or a physiologically acceptable salt thereof can be used as a platelet aggregation inhibiting or controlling agent, spasmolytic agent, therapeutic agent for skin ulcer, peripheral circulation improving agent for limbs and differentiation inducing and promoting agent.

4 Claims, No Drawings

PHARMACEUTICAL USE OF FORSKOLIN DERIVATIVES

This application is a continuation of application Ser. No. 08/425,217 filed Mar. 16, 1995,(abandoned), which is a continuation of application Ser. No. 08/179,366 filed Jan. 10, 1994 (abandoned), which is a divisional of application Ser. No. 08/005,863 filed Jan. 13, 1993 (abandoned), which is a continuation of application Ser. No. 07/670,063 filed Mar. 15, 1991 (abandoned).

BACKGROUND OF THE INVENTION

Field of the Invention

The present invention relates to novel pharmaceutical use of forskolin derivatives represented by the general formula:

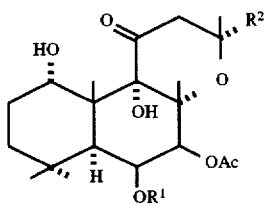

wherein $R^1$, $R^2$ and Ac are as defined later.

Description of the Prior Art

Forskolin having the above formula wherein $R^1$ is hydrogen and $R^2$ is vinyl group is already known to have ionotropic, hypotensive and adenylate cyclase-stimulating actions (cf. JP-A-52-79015 and Arzneimittelforschung, 31, 1248, 1981).

The forskolin derivatives used in the present invention are also disclosed in prior art literature, e.g. EP-A-222413. Regarding the pharmaceutical use of the forskolin derivatives, said literature makes mention of their usefulness as "a remedy for chronic cardiac failure, hypotensive agent, and cerebral vasodilator, and in addition as a remedy for diseases, such as glaucoma, asthma, immunity failure, tumor, and digestive system diseases, which are caused by abnormal regulation of cAMP."

However, no disclosure has ever been made regarding the pharmaceutical use proposed in the present invention.

SUMMARY OF THE INVENTION

The present invention relates to a platelet aggregation inhibiting or controlling agent, spasmolytic agent, therapeutic agent for skin ulcer, peripheral circulation improving agent for limbs and differentiation inducing and promoting agent which contain as active principle a forskolin derivative represented by the formula (I):

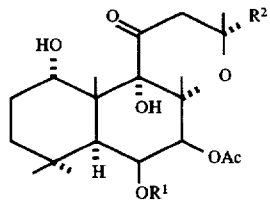

wherein $R^1$ is a group represented by the formula

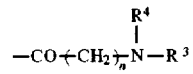

(wherein $R^3$ and $R^4$ are each hydrogen or lower alkyl group, or $R^3$ and $R^4$ may be combined to represent lower alkylene group which may have oxygen or nitrogen atom in the linking chain, and n is an integer of 1 to 5); $R^2$ represents hydrocarbon group having 2 to 3 carbon atoms; and Ac represents acetyl group, or a physiologically acceptable salt thereof.

DETAILED DESCRIPTION OF THE INVENTION

With reference to the general formula (I), $R^3$ and $R_4$ in the formula

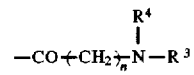

represented by $R^1$ in said formula (I) are each hydrogen or a $C_{1-4}$ lower alkyl group such as methyl, ethyl, propyl, butyl and the like, and when $R^3$ and $R^4$ are combined to represent a lower alkylene group which may have oxygen or nitrogen atom in the linking chain, there can be cited pyrrolidine, piperidine and morpholine as the examples of said lower alkylene group.

Examples of the groups represented by $R^1$ in the general formula (I) are dimethylaminoacetyl group, dimethylaminopropionyl group, dimethylaminobutyryl group, dimethylaminopentanoyl group, dimethylaminohexanoyl group, aminopropionyl group, aminobutyryl group, aminopentanoyl group, aminohexanoyl group, pyrrolidinoacetyl group, piperidinopropionyl group, and morpholinoacetyl group.

Examples of the groups represented by $R^2$ include vinyl group, ethyl group and cyclopropyl group.

As for the forskolin derivatives usable in this invention, they include, for example, 6-(3-dimethylaminopropionyl)forskolin, 6-(4-dimethylaminobutyryl)forskolin, 6-(5-dimethylaminopentanoyl)forskolin, 6-(6-dimethylaminohexanoyl)forskolin, 6-(3-aminopropionyl)forskolin, 6-(4-aminobutyryl)forskolin, 6-(5-aminopentanoyl)forskolin, 6-(6-aminohexanoyl)forskolin, 14,15-dihydro-6-(3-dimethylaminopropionyl)forskolin, and 14,15-dihydro-6-(4-dimethylaminobutyryl)forskolin. The compounds shown in EP-A-222413 are also usable for the purpose of this invention.

In use of the compounds of the formula (I) as a platelet aggregation inhibiting agent, peripheral circulation improving agent for limbs, spasmolytic agent or differentiation inducing and promoting agent, they can be applied either singly or by mixing an excipient or carrier in a suitable form of preparation such as injection, granules, finely divided granules, powder, capsule, suppository, eyewash, patch, ointment, spraying agent, etc. The preparations are administered to the mammals either orally or parenterally.

The excipient and carrier used in the present invention are selected from the pharmaceutically acceptable ones. The kind and composition of such excipient and carrier are decided according to the route and way of administration and other factors. As liquid carrier for instance, there can be used water, alcohols, animal or vegetable oils such as soybean oil, peanut oil, sesame oil, mineral oil, etc., and synthetic oils. As solid carrier, there can be used saccharides such as maltose and sucrose, amino-acids, cellulose derivatives such as hydroxypropyl cellulose, and salts of organic acids such as magnesium stearate.

In the case of injections, it is generally preferred to use physiological saline, various types of buffer solution, solutions of saccharides such as glucose, inositol, mannitol and xylitol, and glycols such as ethylene glycol and polyethylene glycol.

The compounds of this invention may also be worked into a freeze-dried preparation by mixing a saccharide such as glucose, inositol, mannitol, xylitol, maltose, sucrose, etc., and/or an excipient such as phenylalanine, and at the time of application, such preparation may be dissolved in a suitable solution for injection, such as sterile water, physiological saline, dextrose solution, electrolyte solution, and amino-acid solution for intravenous injection.

The content of the compound of the formula (I) in the preparations may vary widely depending on the form of preparation, but usually it is in the range of 0.1 to 100% by weight based on the whole composition. In the case of injections, for instance, it is usually advisable to prepare the solutions so that they contain 0.1 to 5% by weight of a compound (I) of this invention.

For oral administration, the compounds of this invention, mixed with a solid or liquid carrier such as mentioned above, are worked into such forms of preparation as tablet, capsule, powder, granules, liquid, dry syrup and the like. In the case of capsule, tablet, granules and powder, the content of the compound (I) of this invention in the preparations may range usually from about 0.1 to 100% by weight, the balance being the carrier.

The dosage of the compound (I) of this invention is decided by giving consideration to age of the patient, his body weight, state of disease, purpose of treatment and other factors, but usually the recommendable therapeutic dose is 0.001 to 30 mg/kg/day in the case of parenteral administration and 0.003 to 300 mg/kg/day in the case of oral administration.

In case of using the compounds of the formula (I) as a therapeutical agent for cutaneous ulcer, the compound, either singly or mixed with an excipient and/or carrier, is worked into a suitable form of preparation such as powder, spraying agent, emulsion, cream, lotion, ointment or patch (medicated tape, pap, etc.), and the preparation is directly applied to the ulcer surface, preferably the ulcer surface of integument of a mammal. The excipient and carrier used here are selected from the pharmaceutically acceptable ones. The kind and composition thereof are decided according to the route and way of administration and other factors. The content of the compound of this invention in a preparation varies depending on the type (form) of the preparation, but usually it is in the range from 0.001 to 100% by weight based on the whole composition.

The dosage of the compound is determined by giving consideration to age of the patient, his body weight, state of the disease, purpose of treatment and other factors. Generally, however, the therapeutic dose is 0.001 to 300 mg/kg/day, and the preparation is given once to several times a day as occasion demands.

The pharmaceutical use of the compounds of this invention will be described below in terms of test examples using 6-(3-dimethylaminopropionyl)forskolin hydrochloride (this compound being hereinafter referred to as NKH-477) among the compounds of this invention.

Test Example 1-1

The platelet aggregation inhibitory action of NKH-477 was examined on collagen-induced aggregation and ADP-induced aggregation of rabbit blood thrombocyte.

The male Japanese white rabbits (body weight: 2.4–2.8 kg, procured from Tokyo Experimental Animals Co., Ltd.) were divided into groups of 5. The rabbits were etherized and blood was collected from the carotid artery of each rabbit. A 3.8% sodium citrate solution (final concentration: 0.38%) was added to a portion of blood collected from each group of rabbits to obtain platelet rich plasma (PRP). The remaining portion of blood was centrifuged at 3,000 r.p.m. for 15 minutes to obtain platelet poor plasma (PPP). First, permeability of PRP and PPP was determined by using an aggregometer (RMA-31 mfd. by Rika Denki Kogyo K. K.) and set at 0% and 100%, respectively. Separately from the above operation, 250 µl of PRP was placed in a cuvette and after preliminary heating at 37° C. for 2 minutes, 20 µl of specimen was added and incubated under stirring for 2 minutes. Then 10 µl of ADP (Sigma, final conc.: $3 \times 10^{-6}$M) or collagen (Hormon-Chemie, final conc.: 10 µg/ml) was added and the transmission rate was measured. The maximum transmission rate observed in this operation was termed as the maximum aggregation rate. Recording in this operation was conducted on an ink-written recorder (B-381L mfd. by Rika Denki Kogyo K. K.).

NKH-477 was dissolved in a physiological saline to make concentrations of $10^{-8}$ to $10^{-5}$M. Forskolin dissolved in ethanol was used as control.

The results are shown in Table 1-1. It was confirmed that ethanol per se was devoid of platelet aggregation inhibitory action.

TABLE 1-1

|  | Platelet aggregation inhibitory action ($IC_{50}$) | |
| --- | --- | --- |
|  | Collagen-induced aggregation | ADP-induced aggregation |
| NKH-477 | $3.02 \times 10^{-7}$ M | $2.34 \times 10^{-7}$ M |
| Forskolin | $3.09 \times 10^{-6}$ M | $6.03 \times 10^{-6}$ M |

(Values are the mean. n = 5)

As seen from the above table, NKH-477 has over 10 times as strong platelet aggregation inhibitory action as forskolin.

Test Example 1-2

A freeze-dried preparation comprising NKH-477 was dissolved in a physiological saline and administered intravenously to four healthy adults at a rate of 0.8 µg/kg/min for one hour. The degrees of ADP-induced aggregation, epinephrine-induced aggregation and collagen-induced aggregation upon end of administration were measured and compared with those before administration (each figure is the average of measurements on the four subjects). The results are shown in Table 1-2.

TABLE 1-2

|  | Before administration | Upon end of administration | Inhibition rate |
| --- | --- | --- | --- |
| ADP-induced aggregation | 68.5% | 57.5% | 21.7% |
| Epinephrin-induced aggregation | 47.0% | 31.8% | 39.6% |
| Collagen-induced aggregation | 70.3% | 45.8% | 38.7% |

The above results attest to the excellent platelet aggregation inhibitory action of NKH-477 in clinical application.

This corroborates utility of the compounds of the formula (I) as a platelet aggregation inhibiting agent which is useful for the treatment of the diseases caused by platelet aggregation such as Buerger's disease, arteriostenosis such as arteriosclerosis obliterans, thrombosis, etc., and for the prevention of impairment or relapse of said diseases.

Test Example 2

The remedial effect of NKH-477 for skin ulcer was ascertained by the following test.

The abdominal region of each of the test animals— male Wister rats (10 weeks old and weighing 350–390 g) divided into groups of 2—was grained and a piece of skin of about 3 cm in diameter was cut off from said abdominal region of each test rat under anesthesia with pentobarbital (40 mg/kg, i.p.) to prepare a whole-stratum skin cut-off model, and it was used as a skin ulcer model. NKH-477 was used as the test compound (specimen) while a physiological saline was used as control. The specimen was dissolved in a physiological saline (1 mg/ml), and 1 ml of the solution was applied directly to the affected region every day, the treated part being covered with gauze fixed in position. The areas of lesion after the lapse of 1 day, 2 days, 3 days and 5 days from start of application of the specimen solution were measured by a digitizer to determine the lesion reduction rate, from which the skin ulcer curative effect of the test compound was evaluated.

The results are shown in Table 2-1.

TABLE 2-1

| | Lesion reduction rate (%) in whole-stratum skin cut-off model | | | | |
|---|---|---|---|---|---|
| | Days elapsed | | | | |
| Specimen | 0 | 1 | 2 | 3 | 5 |
| Control | — | 26.4 | 36.9 | 45.5 | 66.8 |
| NKH-477 | — | 31.7 | 50.8 | 56.4 | 79.1 |

(Values are the mean. n = 2)

As seen from the above results, curing of skin ulcer is promoted in the NKH-477 applied groups as compared with the control, indicating an excellent curative effect of the compound against skin ulcer. Thus, clinical use is expected of the compounds of the formula (I) as a novel cutaneous ulcer curative agent which is useful for the treatment of various types of cutaneous ulcer such as ulcus cruris, burn ulcer, postoperative ulcer, autoimmune disease-induced ulcer, traumatic ulcer, diabetic ulcer, radiation ulcer, decubitus, etc., or for the prevention of impairment of said diseases.

Test Example 3

The canine coronary and basilar arteries were extirpated under anesthesia with pentobarbital to prepare the 3 mm wide ring preparation. Each preparation was suspended in a 10-ml organ bath filled with a Krebs-Henseleit solution by applying a static tension of 1.5 g (for the coronary artery) and 1.0 g (for the basilar artery). The nutrient solution was maintained at 37° C. and aerated with a 95% $O_2$/5% $CO_2$ gas. The isometric mascular tension was measured with an FD pickup (TB-611T mfd. by Nihon Kohden K. K.) and recorded on a recorder (TI-104 mfd. by Tokai IRIKA K. K.).

After about 2 hours of equilibrium time, contraction was induced with 30 mM of KCl (for coronary artery) and 35 mM of KCl (for basilar artery), and after contraction was stabilized, NKH-477 was administered cumulatively. The spasmolytic effect was expressed as percentages of the inhibition, with the maximal inhibition obtained with papaverine hydrochloride ($10^{-4}$M) being supposed to have shown 100% inhibition.

The results are shown in Table 3.

TABLE 3

| | Inhibition rate (%) | |
|---|---|---|
| | Coronary artery (n = 6) | Basilar artery (n = 3) |
| NKH477 | | |
| $10^{-9}$ M | 6.1 ± 1.6 | 3.8 ± 2.0 |
| $10^{-9}$ M | 23.3 ± 3.2 | 22.1 ± 3.3 |
| $10^{-9}$ M | 58.8 ± 3.9 | 52.0 ± 5.3 |
| $10^{-9}$ M | 86.7 ± 1.5 | 78.3 ± 1.2 |
| $10^{-9}$ M | 94.5 ± 1.3 | 89.2 ± 0.6 |

(mean value ± standard error)

As seen from Table 3, NKH-477 showed a concentration-dependent inhibitory action against KCl-induced contraction in the coronary and basical arteries. The $IC_{50}$ value of NKH-477 was $6.73±1.45×10^{-8}$M (n=6) for coronary artery and $1.02±0.26×10^{-7}$M (n=3) for basilar artery.

The above results ensure the spasmolytic effect of the compounds of the formula (I) and hint at high possibility of these compounds being used as a remedy for various diseases caused by or relating to vasospasm, such as Raynaud's disease, arterial spastic diseases (acro-cyanosis, reticular congestive blue spot, etc.), or a spasmolytic agent which is useful for remitting vasospasm occurring after subarachnoidal hemorrhage, vasospasm caused by administration of an ergot preparation, etc.

Test Example 4

The peripheral circulation improving action of NKH-477 was examined.

(1) Effect on femoral blood flow in anesthetized dogs was tested.

A non-cannulating probe (FF-030T mfd. by Nihon Kohden K. K.) of an electromagnetic flow meter (MFV-2100 mfd. by Nihon Kohden K. K.) was placed around the left femoral artery of a dog anesthetized with pentobarbital to measure femoral bloow flow rate. The femoral blood flow rate was recorded on an ink-written recorder (WI-681G by Nihon Kohden K. K.).

NKH-477 was dissolved in a physiological saline and injected into the right cephalic vein through a Nelaton's tube.

The results are shown in Table 4-1.

TABLE 4-1

| | NKH477 | | | |
|---|---|---|---|---|
| | 1 µg/kg | 3 µg/kg | 10 µg/kg | 30 µmg/kg |
| Increase in femoral blood flow rate (%) | 7.6± 2.9 | 22.9± 5.2 | 61.7± 17.7 | 62.2± 28.7 |

(mean value ± standard error, n = 6)

As seen from Table 4-1, NKH-477 increased the blood flow rate in the femoral artery dose-dependently by intravenous injection of 1–10 µg/kg.

(2) Effect on peripheral vascular resistance in an anesthetized dogs was examined.

Blood pressure was measured with a pressure transducer (CP-01 mfd. by Century Technology Co.) connected to a polyethylene tube inserted into a right femoral artery of a dog anesthetized with pentobarbital, and the cardiac output was measured according to a thermodilution method by using a dilution type cardiac output counter (MLC-4200 mfd. by Nihon Kohden K. K.) and a 7F thermodilution catheter (TC-704 mfd. by Nihon Kohden K. K.) inserted into the pulmonary artery through the right femoral vein. The total peripheral vascular resistance was determined by dividing the mean blood pressure by the cardiac output.

NKH-477 was dissolved in a physiological saline and infused into a right cephalic vein at rates of 0.15, 0.3 and 0.6 µg/kg/min (flow rate: 0.2 ml/min) for 2 hours by using a continuous injection pump (Model 975C mfd. by Harvard Corp.). For the control, physiological saline was similarly infused at a rate of 0.2 ml/min.

The change with time of the total peripheral vascular resistance in the NKH-477 administered group and in the control group is shown in Table 4-2.

TABLE 4-2

| | Change in total peripheral vascular resistance (%) | | | |
|---|---|---|---|---|
| | | NKH477 (µg/kg/min) | | |
| | Control | 0.15 | 0.3 | 0.6 |
| Time of the start of infusion | | | | |
| 10 min | 2.1 ± 1.5 | −2.7 ± 2.4 | −3.7 ± 2.9 | −18.3 ± 8.6 |
| 30 min | 4.0 ± 2.3 | −6.2 ± 3.7 | −10.4 ± 3.1 | −28.1 ± 5.9 |
| 60 min | 13.8 ± 3.4 | −9.1 ± 5.7 | −10.2 ± 4.1 | −29.0 ± 6.4 |
| 120 min | 20.5 ± 9.2 | −5.7 ± 6.6 | −11.5 ± 4.7 | −28.0 ± 5.4 |
| Time after cessation of the infusion | | | | |
| 30 min | 31.4 ± 13.9 | 7.4 ± 7.4 | 6.7 ± 7.0 | −13.4 ± 7.6 |
| 60 min | 29.1 ± 9.7 | 15.7 ± 10.4 | 17.1 ± 6.0 | −4.1 ± 9.1 |
| 120 min | 26.8 ± 12.5 | 12.8 ± 7.2 | 17.2 ± 9.2 | 11.8 ± 12.9 |

(mean value ± standard error)

As seen from Table 4-2, the total peripheral vascular resistance decreased gradually after the start of infusion of NKH-477. This action was dose-dependent, and the maximal effect was reached in 30 minutes to one hour after start of the infusion and maintained till the end of infusion. This action was substantially restored in 2 hours after cessation of the infusion.

(3) Effect on peripheral vascular resistance in human was examined.

A freeze-dried preparation comprising NKH-477 was dissolved in a physiological saline and continuously administered intravenously to four healthy adults at a rate of 0.4 µg/kg/min for one hour.

The rate of reduction of total peripheral vascular resistance after 40 minutes from the start of administration was determined for each subject from mean blood pressure and cardiac output calculated from Ultrasonic cardiography (UCG). The average reduction rate was 19.7%.

On the other hand, a physiological saline alone was continuously administered intravenously to five healthy adults for one hour, and the rate of reduction of total peripheral vascular resistance was similarly determined for each subject. In this case, the average reduction rate was only 1.7%.

The results from the above tests (1)–(3) point to the peripheral circulation improving action of NKH-477, especially its effect of increasing the blood flow rate in the femoral arteries. These facts confirm the possibility of use of said compound as a remedy for the diseases caused by trouble in peripheral blood circulation in limbs, such as Buerger's disease, arteriosclerosis obliterans, etc., or for treatment of frost bits, chilblain, etc., or prevention of impairment or relapse of said diseases.

Test Example 5

The differentiation inducing effect for the NB-1 cells (a human neuroblastoma strain: cell strain derived from neuroblastoma generated in infantile adrenal gland) was examined.

The NB-1 cells were applied to a 96-well plate at a rate of $2 \times 10^3$ cells/well and precultured for 3 days. After attachment and growth were stabilized, the medium (RPMI 1640+ 10% fetal calf serum+SM.PC) was exchanged and a 10 µl solution of each test compound was added. Then, the cells were kept under constant observation to determine the occurrence or non-occurrence of differentiation. 2 mM (1.037 mg/ml) of dibutyryl cAMP dissolved in RPMI 1640 was used as positive control. NKH-477 and 14,15-dihydro-6-(3-dimethylaminopropionyl)forskolin hydrochloride were dissolved in a physiological saline. Forskolin was dissolved in DMSO and diluted with a physiological saline. The criterion for judgment of morphological change in differentiation is as follows. The figures in the parentheses are the ratio of the differentiated cells to the whole cells.

Criteria for judgement

−: none

±: slight (<20%)

+: medium (20–80%)

++: heavy (>80%)

The results obtained after 4-hour incubation are shown in Table 5. It was confirmed that DMSO was totally devoid of differentiation inducing and promoting action at the concentrations used in this test.

TABLE 5

| | Compound | Dose (µM) | Effect |
|---|---|---|---|
| This invention | NKH477 | 1.56 | ± |
| | | 6.25 | ++ |
| | | 25.00 | ++ |
| | | 100.00 | ++ |
| | 14,15-dihydro-6-(3-dimethylamino-propionyl)forskolin | 1.56 | ± |
| | | 6.25 | ± |
| | | 25.00 | ++ |
| | | 100.00 | ++ |
| Control | Forskolin | 1.56 | − |
| | | 6.25 | − |
| | | 25.00 | ± |
| | | 100.00 | + |
| | Dibutyryl cAMP | 2000.0 | + |

As seen from the above table, the compounds of this invention showed more than 100 times as strong differentiation inducing and promoting action as dibutyryl cAMP. They also showed over 10 times as strong action as forskolin.

From the above results, it will be understood that the compounds of the formula (I) have a strong cellular differentiation inducing and promoting action. They are thus considered to be able to act for reforming the cells having abnormal proliferativeness, such as cancer cells and psoriasis cells, back into the normal cells, and therefore their use as an anticarcinogenic agent or psoriasis curing agent is expected. Also, application of said compounds as a therapeutic agent for muscular dystrophy, lesions of hematopoietic organs and other diseases is anticipated.

Examples

Formulation Example 1
Freeze-dried injection

Purified water was added to 30 parts by weight of NKH-477 to make the total amount of the mixture 2,000 parts. After the compound has been dissolved in purified water, the solution was filtered for sterilization by using a Millipore Filter Type GS. 2 g of the filtrate was put into each of the 10-ml vials and freeze-dried to obtain freeze-dried injections containing 30 mg of NKH-477 per vial.

Formulation Example 2
Granules 50 parts by weight of NKH-477, 600 parts by weight of lactose, 250 parts by weight of crystalline cellulose and 100 parts by weight of hydroxypropyl cellulose with a low degree of substitution were mixed well and the mixture was compacted by a roll type compactor (Roller Compactor®), then pulverized and passed through a screen designed to allow passage of 16- to 60-mesh powder, thereby obtaining the granules containing 50 mg of NKH-477 in one gram of granule.

Formulation Example 3
Tablet 10 parts by weight of NKH-477, 30 parts by weight of potato starch, 150 parts by weight of crystalline lactose, 108 parts by weight of crystalline cellulose and 2 parts of magnesium stearate were mixed by a V type mixer and worked into the tablets each weighing 60 mg and containing 2 mg of NKH-477.

Formulation Example 4
Liquid 0.5 g of NKH-477 and 0.2 g of methyl paraoxybenzoate were dissolved in 100 ml of a physiological saline to form a liquid medicine.

Formulation Example 5
Ointment 0.1 g of NKH-477 was added to 99.9 g of an official hydrophilic ointment and kneaded well, and 5 g of the mixture was packed in a metallic tube to form tube ointment.

Formulation Example 6
Ointment 0.05 g of NKH-477 was added to 99.95 g of official macrogol ointment and kneaded to form an ointment.

Formulation Example 7

1 g of forskolin was added to 99 g of dry corn starch and mixed well to prepare a powder for blowing.

What is claimed is:

1. A therapeutic method for the treatment of a skin ulcer which comprises administering to a mammal having a skin ulcer, a medicament containing as the active principle a forskolin derivative represented by the formula:

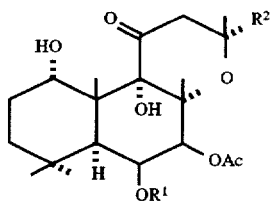

(wherein $R^1$ is a group represented by the formula

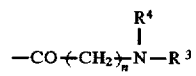

(wherein $R^3$ and $R^4$ are each hydrogen or lower alkyl group, or $R^3$ and $R^4$ may be combined to represent a lower alkylene group which may have an oxygen or nitrogen atom in the linking chain, and n is an integer of 1 to 5); $R^2$ represents a hydrocarbon group having 2 to 3 carbon atoms; and Ac represents an acetyl group) or a physiologically acceptable salt thereof.

2. The method according to claim 1, wherein $R^1$ in the formula is dimethylaminopropionyl group and $R^2$ is vinyl group.

3. The method according to claim 1, wherein the skin ulcer is decubitus.

4. The method according to claim 1, wherein the medicament is applied directly to the region of skin ulcer.

* * * * *